(12) United States Patent
Hughes

(10) Patent No.: US 7,201,841 B2
(45) Date of Patent: Apr. 10, 2007

(54) COMPOSITE MATERIALS FOR FLUID TREATMENT

(75) Inventor: Kenneth D. Hughes, Alpharetta, GA (US)

(73) Assignee: Water Visions International, Inc., Atlanta, GA (US)

( * ) Notice: Subject to any disclaimer, the term of this patent is extended or adjusted under 35 U.S.C. 154(b) by 0 days.

(21) Appl. No.: 10/359,032

(22) Filed: Feb. 5, 2003

(65) Prior Publication Data

US 2004/0149634 A1  Aug. 5, 2004

(51) Int. Cl.
*B01D 35/14* (2006.01)

(52) U.S. Cl. .................. 210/96.1; 210/206; 210/502.1; 210/510.1

(58) Field of Classification Search ............... 210/96.1, 210/500.1, 506, 206; 427/195, 210
See application file for complete search history.

(56) References Cited

U.S. PATENT DOCUMENTS

| | | | |
|---|---|---|---|
| 286,370 A | 10/1883 | Baker | |
| 3,238,056 A | 3/1966 | Pall et al. | |
| 3,344,061 A | 9/1967 | Kellum | |
| 3,375,933 A | 4/1968 | Rodman | |
| 3,442,796 A | 5/1969 | Hayes | |
| 3,545,622 A | 12/1970 | Sakhonvaky | |
| 3,662,893 A | 5/1972 | Humbert | |
| 3,871,881 A | 3/1975 | Mikelsons | |
| 3,996,131 A | 12/1976 | Conn | |
| 4,078,112 A | 3/1978 | Bibeau | |
| 4,079,001 A | 3/1978 | Haase et al. | |
| 4,084,747 A | 4/1978 | Alliger | |
| 4,098,690 A | 7/1978 | Semmens | |
| 4,160,727 A | 7/1979 | Harris, Jr. | |
| 4,167,479 A | 9/1979 | Besik | |
| 4,178,361 A * | 12/1979 | Cohen et al. ............... 424/487 |
| 4,182,676 A | 1/1980 | Casolo | |
| 4,190,576 A | 2/1980 | Thomson et al. | |
| 4,194,040 A | 3/1980 | Breton et al. | |
| 4,198,296 A | 4/1980 | Doumas et al. | |
| 4,230,595 A | 10/1980 | Yamaji et al. | |
| 4,252,571 A | 2/1981 | Reilly | |
| 4,282,094 A | 8/1981 | Mitchell | |
| 4,330,531 A | 5/1982 | Alliger | |
| 4,482,459 A | 11/1984 | Shiver | |
| 4,585,482 A | 4/1986 | Tice et al. | |
| 4,610,790 A | 9/1986 | Reti et al. | |
| 4,623,467 A | 11/1986 | Hamlin | |
| 4,629,464 A | 12/1986 | Takata et al. | |

(Continued)

FOREIGN PATENT DOCUMENTS

JP  59145087 A  8/1984

(Continued)

*Primary Examiner*—Terry K. Cecil
(74) *Attorney, Agent, or Firm*—Sutherland Asbill & Brennan LLP

(57) ABSTRACT

This invention relates generally to composite materials and to devices which may alter fluid parameters. Devices incorporating the composite materials of the invention are used to deliver, remove, and generate, fluid treatment agents, and combinations thereof. These materials and devices are applicable to many different fluid processing situations including drinking water treatment, wastewater treatment, emission treatment, pollution cleanup, and sensing fluid composition. In its more particular aspects, the invention relates to the field of composites that may be widely tailored for many different treatment applications.

45 Claims, 5 Drawing Sheets

U.S. PATENT DOCUMENTS

| | | | |
|---|---|---|---|
| 4,642,192 | A | 2/1987 | Heskett |
| 4,643,182 | A | 2/1987 | Klein |
| 4,645,503 | A | 2/1987 | Lin et al. |
| 4,645,604 | A | 2/1987 | Martinola et al. |
| 4,670,150 | A | 6/1987 | Hsiung et al. |
| 4,683,039 | A | 7/1987 | Twardowski et al. |
| 4,702,836 | A | 10/1987 | Mutoh et al. |
| 4,711,723 | A | 12/1987 | Bray |
| 4,717,566 | A * | 1/1988 | Eckenhoff et al. .......... 424/438 |
| 4,806,244 | A | 2/1989 | Guilhem |
| 4,851,122 | A | 7/1989 | Stanley |
| 4,865,733 | A | 9/1989 | Tsuru et al. |
| 4,874,511 | A | 10/1989 | Kawasaki et al. |
| 4,880,541 | A | 11/1989 | Chiron et al. |
| 4,889,630 | A | 12/1989 | Reinhardt et al. |
| 4,900,444 | A | 2/1990 | Seita et al. |
| 4,902,427 | A | 2/1990 | Szczepanik |
| 4,946,603 | A | 8/1990 | Laugharn et al. |
| 4,988,440 | A | 1/1991 | Bernard et al. |
| 5,019,311 | A | 5/1991 | Koslow |
| 5,071,610 | A | 12/1991 | Hagen et al. |
| 5,082,568 | A | 1/1992 | Holler |
| 5,085,781 | A | 2/1992 | Tsuru et al. |
| 5,089,119 | A | 2/1992 | Day et al. |
| 5,118,655 | A | 6/1992 | Pedersen |
| 5,122,274 | A | 6/1992 | Heskett |
| 5,127,411 | A | 7/1992 | Schoolman et al. |
| 5,135,654 | A | 8/1992 | Heskett |
| 5,143,752 | A | 9/1992 | Nakajima et al. |
| 5,147,722 | A | 9/1992 | Koslow |
| 5,149,437 | A | 9/1992 | Wilkinson et al. |
| 5,156,739 | A | 10/1992 | Dawson et al. |
| 5,161,686 | A | 11/1992 | Weber et al. |
| 5,180,491 | A | 1/1993 | Polasky |
| 5,189,092 | A | 2/1993 | Koslow |
| 5,198,118 | A | 3/1993 | Heskett |
| 5,205,928 | A | 4/1993 | Inoue et al. |
| 5,215,657 | A | 6/1993 | Goldfield et al. |
| 5,238,574 | A | 8/1993 | Kawashima et al. |
| 5,249,948 | A | 10/1993 | Koslow |
| 5,266,203 | A | 11/1993 | Mukhopadhyay et al. |
| 5,271,848 | A | 12/1993 | Smith et al. |
| 5,298,205 | A | 3/1994 | Hayes et al. |
| 5,331,037 | A | 7/1994 | Koslow |
| 5,338,766 | A | 8/1994 | Phan et al. |
| 5,346,565 | A | 9/1994 | White |
| 5,360,609 | A | 11/1994 | Wellinghoff |
| 5,384,047 | A | 1/1995 | Scheckler et al. |
| 5,415,759 | A | 5/1995 | Cawlfield et al. |
| 5,422,340 | A | 6/1995 | Ammann et al. |
| 5,482,773 | A | 1/1996 | Bair |
| RE35,267 | E | 6/1996 | Tsuru et al. |
| 5,552,046 | A | 9/1996 | Johnston et al. |
| 5,580,749 | A | 12/1996 | Hughes |
| 5,589,066 | A | 12/1996 | Gray |
| 5,597,487 | A | 1/1997 | Vogel et al. |
| 5,635,071 | A | 6/1997 | Al-Samadi |
| 5,651,884 | A | 7/1997 | Ichitsuka et al. |
| 5,656,140 | A | 8/1997 | Oesterle et al. |
| 5,670,053 | A | 9/1997 | Collentro et al. |
| 5,676,745 | A | 10/1997 | Kelly et al. |
| 5,681,447 | A | 10/1997 | Maycock et al. |
| 5,688,378 | A | 11/1997 | Khoe et al. |
| 5,728,157 | A | 3/1998 | Prescott |
| 5,750,026 | A | 5/1998 | Gadkaree et al. |
| 5,755,969 | A | 5/1998 | Okamoto |
| 5,770,416 | A | 6/1998 | Lihme et al. |
| 5,792,513 | A | 8/1998 | Koslow et al. |
| 5,866,003 | A | 2/1999 | Okubo et al. |
| 5,882,517 | A | 3/1999 | Chen et al. |
| 5,935,887 | A | 8/1999 | Sudo et al. |
| 5,961,843 | A | 10/1999 | Hayakawa et al. |
| 5,977,003 | A | 11/1999 | Wilshaw et al. |
| 5,977,829 | A | 11/1999 | Wells |
| 6,054,050 | A | 4/2000 | Dyke |
| 6,054,059 | A | 4/2000 | Latimer, Jr. et al. |
| 6,103,125 | A | 8/2000 | Kuepper |
| 6,110,375 | A | 8/2000 | Bacchus et al. |
| 6,117,333 | A | 9/2000 | Frankiewicz et al. |
| 6,156,186 | A | 12/2000 | Mueller et al. |
| 6,162,361 | A | 12/2000 | Adiga |
| 6,180,016 | B1 | 1/2001 | Johnston et al. |
| 6,187,192 | B1 | 2/2001 | Johnston et al. |
| 6,187,200 | B1 | 2/2001 | Yamamura et al. |
| 6,190,556 | B1 | 2/2001 | Uhlinger |
| 6,197,193 | B1 | 3/2001 | Archer |
| 6,203,688 | B1 | 3/2001 | Lipsztajn et al. |
| 6,238,643 | B1 | 5/2001 | Thangaraj et al. |
| 6,274,041 | B1 | 8/2001 | Williamson et al. |
| 6,290,686 | B1 | 9/2001 | Tanzer |
| 6,312,598 | B1 | 11/2001 | Munson et al. |
| 6,355,093 | B1 | 3/2002 | Schwartz et al. |
| 6,368,510 | B2 | 4/2002 | Friot |
| 6,376,011 | B1 | 4/2002 | Reeves et al. |
| 6,395,678 | B1 | 5/2002 | Summers et al. |
| 6,428,696 | B2 | 8/2002 | Kuke |
| 6,432,322 | B1 | 8/2002 | Speronello et al. |
| 6,451,253 | B1 | 9/2002 | Pitochelli et al. |
| 6,458,162 | B1 | 10/2002 | Kovlish et al. |
| 6,458,735 | B1 | 10/2002 | Klatte |
| 6,461,514 | B1 | 10/2002 | Al-Samadi |
| 6,464,672 | B1 | 10/2002 | Buckley |
| 6,468,942 | B1 | 10/2002 | Sansalone |
| 6,503,419 | B2 | 1/2003 | Klatte |
| 6,522,141 | B2 | 2/2003 | Debbins et al. |
| 6,552,141 | B1 * | 4/2003 | Chmelir et al. ............. 526/217 |
| 6,575,961 | B2 * | 6/2003 | Joshi ...................... 604/891.1 |
| 6,605,304 | B1 | 8/2003 | Wellinghoff et al. |
| 6,607,668 | B2 | 8/2003 | Rela |
| 6,677,256 | B1 | 1/2004 | Li et al. |
| 6,712,974 | B1 | 3/2004 | Palm et al. |
| 6,821,435 | B1 | 11/2004 | Lindquist et al. |
| 6,833,075 | B2 | 12/2004 | Hughes |
| 6,861,002 | B2 | 3/2005 | Hughes |
| 6,878,285 | B2 | 4/2005 | Hughes |
| 6,957,743 | B2 | 10/2005 | Johnston et al. |
| 2002/0006427 | A1 | 1/2002 | Umezu et al. |
| 2002/0158007 | A1 | 10/2002 | Li |
| 2003/0173287 | A1 | 9/2003 | Johnston et al. |
| 2003/0196955 | A1 | 10/2003 | Hughes |
| 2004/0159605 | A1 | 8/2004 | Hughes |
| 2004/0232068 | A1 | 11/2004 | Johnston et al. |
| 2005/0098495 | A1 | 5/2005 | Hughes |

FOREIGN PATENT DOCUMENTS

| JP | 62204892 | 9/1987 |
|---|---|---|
| WO | WO 99/26987 | 6/1999 |
| WO | WO 02/30766 | 4/2002 |

* cited by examiner

COMPOSITE MATERIALS FOR FLUID TREATMENT

BACKGROUND OF THE INVENTION

1. Field of the Invention

This invention relates generally to composite materials and to devices that may alter fluid parameters. Devices incorporating the composite materials of the invention are used to deliver, remove, and generate fluid treatment agents (naturally occurring and synthetic chemical and biological agents), and combinations thereof. These materials and devices are applicable to many different fluid treatment situations including those targeting drinking water, process fluids, fuels and emission, beverage production, cleaning operations, and sensing fluid composition. In its more particular aspects, the invention relates to the field of multi-functional composite materials that may be tailored for many different fluid treatment applications.

2. Description of Related Art

Common Fluid Treatment Art

The treatment of fluids involves the removal of dissolved or suspended contaminants, the modification of fundamental parameters such as pH, dissolved gases, dissolved solids content, and temperature, and the incorporation of chemical and biological agents. Standard fluid treatment practice directed at these goals involves the use of many different treatment agents, devices, and techniques. Treatment agents are commonly applied in all three states, gas, liquid, and solid. The nature of the contaminant that must be removed or agent that must be added and the allowable cost of the operation controls the choice of treatment, agent, device, and methods used. Fluids are treated for a wide range of applications including breathing, cleaning, ingestion, cooling, and direct participation in industrial chemical and biological processes.

Delivery of Fluid Treatment Chemicals

Fluid treatment agents are added to fluids to remove contaminants, chemically convert contaminants, and to modify fluid parameters including pH and the composition of dissolved components. For example, chlorine containing compounds are useful for disinfecting fluids and the containers and conduits used to manage the fluids.

Depending upon the scale of the application, the technical experience of personnel conducting the treatment process, and the allowable costs, either solid, liquid, or gaseous forms of chlorine are used. Additional fluid treatment examples include the dosing of flocculating agents to remove small particulate matter suspended in a fluid and the injection of carbon dioxide for beverages production.

Delivery of solid, liquid or gaseous fluid treatment agents to fluids is complicated and requires significant technical experience to complete safely and efficiently. Injection and dosing systems require the combination and optimization of well characterized solutions of treatment agents, pumps, piping or tubing, flow control devices including valves, and often a power source. Typically, the equipment costs and technical skill required to install, operate, and maintain injection and dosing equipment limits the number of suitable application sites. Additionally, incorrect setting of equipment often damages or substantially decreases the lifetime of equipment positioned downstream of the dosing operation.

Furthermore, many dosing and injection operations utilize reservoirs containing concentrated forms of the treatment agents. These reservoirs may pose safety hazards to both personnel who operate the equipment or those in the vicinity and to equipment that contacts these agents. Spills, splashing, and leaks often require specialized cleanup agents, procedures, and often a distinct team of specially trained personnel. As a result, all fluid dosing and injection systems require constant supervision in order to effectively maintain operations.

Chemical Generation and Delivery

Several important fluid treatment agents may not be stored effectively and must be generated at the location of treatment. Examples include, the on-site generation of chlorine dioxide and ozone. Both are valuable oxidizing agents that may disinfect, breakdown organic compounds, and react with dissolved inorganic compounds. Flocculating agents based on hydroxide precipitates including those containing aluminum and iron are also commonly generated on site to maximize their particulate removal efficiencies. Safety is also a consideration. Transport of reaction precursors in pressurized and concentrated forms is typically hazardous and a significant drawback to the technology.

Chemical and Biological Agent Collection, Sampling, and Detection

There are certain fluid contaminants that pose a hazard at extremely low concentrations. Examples include biological agents, nerve agents, and heavy metals. Since many of these contaminants accumulate in the body and fluid treatment components over time it is important to employ detection methods that are sensitive to very low concentrations of these agents. Commonly some type of contaminant concentrating technique is used to retain and accumulate the agent to facilitate qualitative as well as quantitative analysis. Both solid phase adsorption and liquid based extraction techniques are used for removing contaminants from the fluid and concentrating. Analysis of the concentrated contaminant(s) may involve stripping the contaminant from the concentrating medium, analyzing the collection media directly, or combinations thereof.

Application Space

A wide range of industrial processes and consumer activities involve the use of fluids. In all cases fluids must be tailored for the specific application. These fluids are either prepared and packaged for direct use or equipment and products are fabricated that modify the fluid for its desired purpose at the point of use. Beverage products prepared for ingestion require fluids to be initially purified and then formulated with agents to impart flavor, color, or nutritional benefit. Examples include commercially available ready-to-drink beverages as well as tap water that is treated before entering a complex distribution system. Similar situations exist for pharmaceutical and medical solution preparation.

Many companies produce products that treat gases and liquids at the point of use or the point of entry into an industrial facility, a residence, or the environment. Common examples include breathing air and drinking water. Treatment products for these fluids vary tremendously in function, scale, and cost. In recent years, the desire for air filtration in the home has become more popular as a need has been demonstrated. Products with increasing sophistication are now available, addressing the concerns of both energy efficiency and indoor air quality. Many breathing air and drinking water applications share contaminant types and removal requirements.

Consumers use many types of household chemicals to modify fluids for cleaning in and around the household. Consumers also use many types of solutions for maintaining health and appearance including solutions specialized for eye care, lens care, dental care, and oral care. Additionally, leisure water activities including the use of pools and spas require fluid treatment on a continual basis.

Many industries must treat influent and effluent fluids in bulk. In general, both air and water emissions from industry must be of a higher quality than the original source. These include those that treat drinking water, prepare food and beverages, generate power, control equipment temperature, process chemical and biological agents including fermentation processing and petroleum component separation. Pharmaceutical and medicinal solutions of gases and liquids require both purification and active agent incorporation. Similarly, the removal of contaminants from breathable air in hospitals and clean rooms, where ultrapurified air is required, and in environments where air is recirculated, such as aircraft, spacecraft, individual protective suits, small group protective structures, and automobiles, is also an important application for fluid treatment.

New materials and devices that may improve the function and capacity of standard treatment operations as well as increase the safety and cost effectiveness are highly desired.

SUMMARY OF THE INVENTION

To this end, novel composite materials and methods for fabricating these composite materials have been discovered. These materials and devices containing these materials incorporate the beneficial aspects of both solid and liquid fluid treatment agents. The method and process of the invention facilitates the generation of a wide range of composite materials and devices including those which may be used for, removing dissolved and suspended contaminants, chemically reacting with dissolved or suspended contaminants, delivering chemical and biological agents, generating dissolved agents for further application, generating solids, liquids, and gases for a broad range of applications. Likewise, the materials and devices of the invention facilitate concentrating, storing, detecting, and degrading contaminants that are present in gases, liquids, and aerosols, at very low concentrations.

The composite materials and devices of the invention may be used in a manner that directs or controls fluid flow and composite material contact. Specifically, by controlling the composition of the material, fluid may be directed through the material, across the surface of the material, or a combination thereof. Manipulating flow rates allows contact time between fluid and composite to be controlled, and the selectivity of treatment application.

Composite materials and devices of the invention may be generated in widely varying shapes and sizes, and with functions that may be infinitely tailored and tuned for specific applications. The invention is scale independent as it may be utilized in very large as well as very small applications. The materials and devices of the invention may contain a broad range of fluid treatment agents for treating gases, liquids, and aerosols. Likewise, these materials and devices may contain a broad range of fluid additives commonly delivered into fluids for industrial and consumer application.

The composite materials and methods of producing materials and devices of the invention, incorporate solid materials that have both fluid absorbing and fluid expanding characteristics. These materials may be used independently or combined with materials that do not expand when exposed to fluids. Composite materials may be generated by combining fluid expanding solids and single composition liquids, by combining fluid expanding solids and liquid mixtures, by combining fluid expanding solids and liquids with dissolved or suspended agents, by combining fluid expanding solids and liquid mixtures which, when exposed to solids, liquids, or gases, generate insoluble agents, by combining fluid expanding solids and liquid mixtures which are then exposed to solids, liquids, or gases generate liquids or gases, by combining fluid expanding solids and liquid mixtures that generate soluble agents, insoluble agents, and combinations thereof, when exposed to radiation or thermal energy. The composite materials may carry chemical and biological agents in the fluid used to expand the solid, on the materials surface, or a combination thereof. Composite materials may be further tailored by incorporating material that does not expand substantially in the presence of fluid. These non-expanding materials may serve multiple functions in the composite including spacing, pore generation, fluid storage and fluid treatment.

The materials and processes of the invention may be used to prepare a wide range of devices with significant consumer, industrial, space, humanitarian, and defense application. In preferred applications the composite materials are fabricated in the form of blocks, tubes, sheets, fibers, films, or as isolated particles and are used to, modify the properties of fluids through agent removal, conversion, addition, or a combination thereof, and sensing of fluid composition. The materials and methods of the invention provide a means of combining many standard fluid treatment operations, processes, and materials into a single composite material. In many cases, the efficiency, safety, and economics of the treatment process are improved. The materials and methods of the invention allow greater device design flexibility that ultimately allows devices of new shapes and sizes to be applied in new locations as well as to better fit into current application space. Equally important is the manufacturing flexibility that the materials and methods of the invention enable. Materials and devices may be fabricated and assembled by hand or adapted to high throughput equipment. The cost associated with materials and manufacturing may be adapted to many manufacturing environments and situations. Additionally, devices may be prepared on the go, in the field, and in many cases serviced in a similar manner.

As indicated above, many types of solid-liquid combinations may be generated with the materials and method of the invention. These materials and devices incorporating these materials are immediately useful in a broad range of fluid treatment applications. The materials and methods of the invention greatly simplify the removal and delivery of chemical and biological agents associated with fluids. Further the materials and methods of the invention provide the capacity to simultaneously employ both solids and liquids in the treatment of fluids. Furthermore, the devices and methods of the invention improve the safety, and reduce the complexity of many fluid treatment agent dosing and injection operations. The solids incorporated into the composite materials of the invention may be used for absorption, adsorption, chemical reaction, dissolution, and a combination thereof. The liquids incorporated into the composite materials of the invention may be used for absorption, adsorption, chemical reaction, dissolution and a combination thereof. The combination of solids and liquids provides a platform for tailoring treatment materials where the solids and liquids function synergistically.

A wide range of contaminants may be treated with the materials and methods of the invention. These include naturally occurring and synthetic organic and inorganic agents, in both dissolved and particulate states, microorganisms in active and dormant states, and combinations thereof.

Agents that may be delivered to fluids include naturally occurring and synthetic organic and inorganic agents in dissolved and particulate states, microorganisms in active and dormant states, and combinations thereof.

The applications for the materials and devices of the invention may be roughly separated into two groups for description purposes but in no manner limits the applications and fields where the materials and devices of the invention are useful. In many cases, similar materials and devices of the invention may be applied directly in both gas phase and liquid phase applications.

The first group is the treatment of liquids including those associated with drinking water, waste water, beverage production, pharmaceutical and semiconductor processing, chemical processing, biotechnology product processing, process streams that use catalysts, cleaning solution preparation, eye and lens care, dental and oral care, and toxin concentration, detection, and degradation.

The second group is the treatment of gases including those associated with breathing air, residential air, industrial emissions, energy production, enclosed recirculated air systems, process streams that use catalysts, and toxin concentration and detection.

In typical embodiments, the invention relates to a composite material for fluid treatment that consists of a fluid expandable material such as a natural or synthetic polymer or clay that carries a fluid with a composition that is typically different than the fluid undergoing treatment. The fluid contained by the expandable material and therefore the composite material may or may not be removed from the composite material in the fluid treatment operation.

Typical embodiments may also include composite materials that are generated from a mixture of fluid expanding and fluid nonexpanding materials. The nonexpanding materials provide a dilution function, may affect porosity, and may also provide an extension of the composite material's fluid treatment function. Additionally, synergistic combinations and complex multistage treatment functions are possible. Non-expanding solid materials include carbon, activated carbons, natural and synthetic minerals, textiles, ion-exchange materials, resins, metals, catalysts, synthetic and natural molecules and polymers, and a wide range of materials typically used in fluid treatment.

Typical embodiments may also include composite materials that contain fluid soluble chemical and biological agents that provide a fluid treatment function. Specifically, these agents are used to remove contaminants or modify the composition of the fluid contacting the material. The soluble agent may be included in the composite in a dissolved or solid form.

Typical embodiments may also include composite materials that contain fluid insoluble or slightly soluble chemical and biological agents that provide a fluid treatment function. Specifically, these agents are used to remove contaminants or modify the composition of the fluid contacting the material.

Typical embodiments may also include a support structure for the composite materials. The supports are porous in defined locations and designs and prepared from rigid, semi-rigid, or flexible materials and combinations thereof. These supports may be prepared from synthetic as well as natural materials.

Typical embodiments may also include a housing for the composite materials and associated support structures, if any, as well as a passive or active system or mechanism for directing fluid into contact with the composite materials. Examples would include deflectors, foils, pumps, blowers, and cyclones. These may also be combined with electric charging devices and precipitating devices.

Typical embodiments may also include situations where the agents contained by the composite material of the invention react through exposure and contact with other agents in solid, liquid, or gaseous form and generate additional solid, liquid, or gaseous fluid treatment agents. The combination of these agents and materials and the devices that control their contact are representative of devices of the invention.

Typical embodiments may also include situations where the chemical or biological agents removed from a contaminated fluid are accumulated (concentrated) over time for the purpose of fluid purification and contaminant identification and quantitation. The materials and devices of the invention are ideally suited for direct or indirect chemical and genetic analysis, non-destructive and destructive spectroscopic analysis, as well as other types of chemical analysis. Materials and devices of the invention facilitate analysis in the laboratory as well as in the field with a range of electronic and radiation based sensing methods.

Typical embodiments may also include situations where the composite material serves as a tunable conduit between the fluid to be treated and a reservoir. The reservoir may contain fluid treatment agents for delivery to the fluid requiring treatment, or it may serve as a collector for transfer of agents from the fluid requiring treatment, or combinations thereof.

Typical embodiments for composite form may also include, blocks, sheets, webs, membrane, fibers, and individual particles or fibers that may be moved through a fluid in continuous or semi-continuous fashion. Translation methods may include mechanical, magnetic, and electric field manipulation, the use of gravity, or combinations thereof.

BRIEF DESCRIPTION OF THE DRAWINGS

FIG. 2B includes an extension of the central bore outside of the composite material. By adjusting the length of this extended central bore fluid composite material contact may be controlled. Choice of cartridge housing porosity may also be used in conjunction with central bore location to fine tune fluid treatment parameters. The cartridge housing is contained in a larger vessel that connects to tanks and conduits that direct fluid flow in and out of the vessel.

FIG. 3b extends the embodiment to include the wrapping of planar sheets containing the materials of the invention around a central bore. This geometry allows cross-flow as well as flow through in a radial geometry.

FIG. 4A presents the embodiment in a rectangular format while 4B presents the embodiment in a cylindrical format. In both orientations the dropped particles may also be guided using fibers, meshes, or screens. This embodiment is easily extended to fibers and sheets that are pulled manipulated the fluid contact zone.

DETAILED DESCRIPTION OF THE INVENTION

Figure 1A:
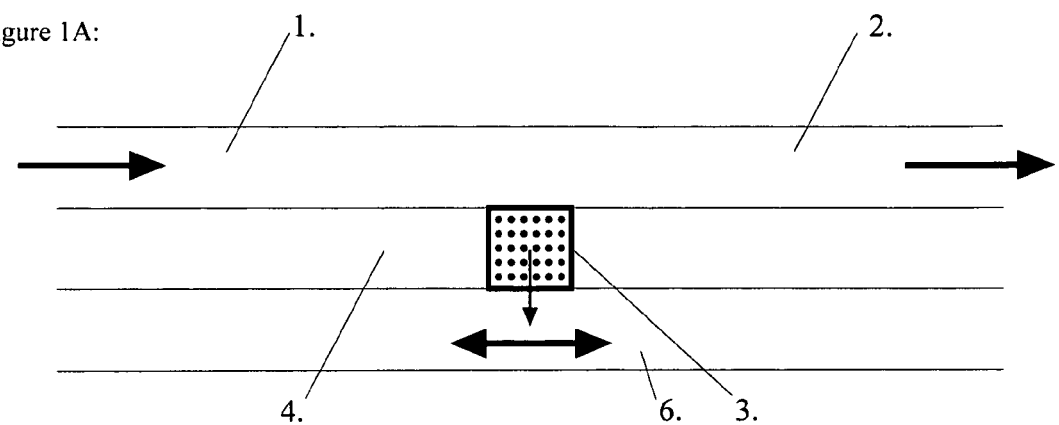
FIG. 1A is a cross-sectional view illustrating a particular embodiment of the invention, namely a porous support (two-sides) containing composite material comprising fluid expandable material, expanded with a fluid treatment agent and combined with an optional fluid non-expanding material. An appropriate housing is positioned in a cross-flow filtration geometry that connects a conduit containing the fluid to be treated and a conduit or container that collects and transfers treated fluid.

As indicated above in the Summary, in its general embodiments the invention relates to composite materials and devices incorporating the composite materials that combine fluids and fluid expandable materials. General embodiments also include the mixture of fluid expandable and non-fluid expandable materials into composites. Devices based on these general embodiments may be fabricated by adding the fluid expanding and optionally non-expanding materials to porous containers or supports and subsequently to housings that provide fluid contact. These porous containers may take the form of canisters, coatings, membranes, and sheets and may be combined, wrapped, or prepared in a wide range of geometric structures. Devices may be produced in any shape or size and may be rigid or flexible. The materials of the invention may be utilized in direct contact with membrane materials including those incorporating hollow fibers.

Fluid flow through or across the composite material may be tuned by the selection of components, size of the granular or fibrous fluid expanding and optional nonexpanding components and the porous structural support, if necessary for the application. As used herein, the term "composite material" does not denote any particular geometrical shape. Nonlimiting examples of "composite materials" as this term is intended to be used include tubes and annular rings, as well as more conventional geometrical solids. Material formed into flexible composite materials is particularly suitable for use in pipes or tubes that serve as the fluid filter medium and in combination with membrane systems including hollow fiber systems.

One of the desirable features of composite materials generated with the invention is that devices may be formed into any desired shape. This provides ease of handling and extremely high scalability. For example, a composite material may be formed into a monolith or wrapped sheet that fits into conventional fluid treatment housings. It may be shaped to provide fluid treatment as part of a portable or personal system or shaped to provide emission treatment for large industrial sites. The material may be formed into several different pieces, through which fluid flows in series or in parallel. Sheets or membranes of the composite purification material may also be formed. The rigidity of the purification material and subsequent devices, whether in block form or in sheet/membrane form, may be altered through inclusion of flexible support structures that contain the expanding and optional non-expanding material.

The expanding material may be in the form of particles ranging in size from 0.05 microns through 100 millimeters, fibers with diameters of 0.05 microns through 100 millimeters, or combinations thereof. The optional non-expanding material may have similar sizes.

Preferred and applicable expanding fluid treatment matter includes material that expands as a result of absorption of fluids (either gases or liquids) and may be generated from a range of synthetic and natural materials. These materials include synthetic and natural polymers, as well as certain natural and synthetic clays.

The class of materials known as "superabsorbents" is particularly suitable in this regard. Superabsorbents are natural, synthetic, or mixed polymers that are not fully cross-linked. They may be classified as polyelectrolyte or nonpolyelectrolyte types as well covalent, ionic, or physical gelling materials. These materials have the capacity to absorb many times their own volume in fluid. Examples of synthetic materials include polyacrylic acids, polyacrylamides, poly-alcohols, polyamines, and polyethylene oxides. The composite superabsorbent material may also be selected from derivatives of polyacrylic acids, polyacrylamides, poly-alcohols, polyamines, polyethylene oxides, cellulose, chitins, gelatins. starch, polyvinyl alcohols and polyacrylic acid, polyacrylonitrile, carboxymethyl cellulose, alginic acids, carrageenans isolated from seaweeds, polysaccharides, pectins, xanthans, poly-(diallyldimethylammonium chloride), poly-vinylpyridine, poly-vinylbenzyltrimethylammonium salts, polyvinylacetates, polylactic acids, or combinations thereof. The composite material may also comprises a material selected from resins obtained by polymerizing derivatives of acrylic acid or resins obtained by polymerizing derivatives of acrylamide.

Biodegradable materials that are suitable include cellulose derivatives, chitins, and gelatins. Additionally mixtures of synthetic polymer and natural polymers either as distinct chains or in copolymers may be used to generate these absorbent materials. Examples include starch polyacrylic acid, polyvinyl alcohols and polyacrylic acid, starch and polyacrylonitrile, carboxymethyl cellulose, alginic acids carrageenans isolated from seaweeds, polysaccharides, pectins, xanthans, poly(diallyldimethylammonium chloride), polyvinylpyridine, polyvinylbenzyltrimethylammonium salts, cellulose, alginic acids, carrageenans isolated from seaweeds, polysaccharides, pectins, xanthans, starch, or combinations thereof, polyethyleneglycol, a polylactic acid, a polyvinylalcohol, a co-polylactideglycolide, cellulose, alginic acids, carrageenans isolated from seaweeds, polysaccharides, pectins, xanthans, and starch.

As those experienced in the art will understand the process of crosslinking polymer chains derived from either any source or combinations of sources, are variable and will affect the magnitude of fluid absorption, and the types of fluids that may be absorbed.

Additionally those experienced in the art will understand that molecular characteristics such as polymer chain composition, functional group position and distribution as well as polymer molecular weight and distribution will effect performance, and will know how to modify these parameters to vary the properties of the resulting composite consistent with the basic tenets of the invention. Further those experienced in the art will understand the expansion or final volume capacity of a material is also subject to the type and composition of the fluid in which the material is exposed.

Inorganic sources of expanding particles include aluminosilicates, smectic or montmorillinite clays, and a preferred clay, bentonite.

Preferred and applicable optional non-expanding materials include naturally occurring, synthetic, and recycled materials. Suitable optional non-expanding materials include insoluble phosphate containing minerals selected from calcium phosphates, iron phosphates, manganese phosphates, aluminum phosphates, magnesium phosphates, magnesium phosphates, silver phosphates, copper phosphates, zinc phosphates, zirconium phosphates, calcium monophosphates, diphosphates, tricalicum phosphates, octaphosphate, metaphosphates, metal oxides selected such as aluminum oxides, iron oxides, magnesium oxides, calcium oxides, manganese oxides, zinc oxides, copper oxides, titanium oxides, silicon oxides, aluminum containing minerals such as, alumina bauxite, kaoline, iron containing minerals such as iron oxide amorphous hydrous ferric oxide, maghemite, hematite, goethite, lepidocrocite, manganese containing minerals such as, manganese oxide, pyrolusite, silica containing minerals including, silica, quartz, metals such as iron, copper, manganese, silver, gold, platinum, rhodium, zinc, alloys prepared from iron, copper, zinc, carbon, chromium, manganese, nickel, carbonates such as calcium carbonate, magnesium carbonate, iron carbonate, aluminum carbonate, sulfates including magnesium sulfate, and calcium sulfate, hydroxides such as aluminum hydroxide, iron hydroxide, magnesium hydroxide, calcium hydroxide, and copper hydroxide. Synthetic and natural fibers, including strings, yarns and textiles including, cotton, wool, polypropylene, rayon, polyester, nylon, acrylic are also applicable. Ion exchange material is a preferred material and includes resins selected from functionalized styrenes, vinylchlorides, divinyl benzenes, methacrylates, acrylates, or mixtures, copolymers, and blends thereof. Natural and synthetic zeolites such as clinoptilolite and glauconate are preferred.

Catalytic materials generated from these components are quite common and these are applicable in all known forms. Those experienced in the art will recognize that the deposition of molecules containing active sites that include metals and atoms and nanocomposites of metals and semi-metals on the surface of support materials are immediately applicable.

Fast and slowly dissolving as well as time release materials are also available in particulate and fiber form and these are applicable as non-expanding materials. Preferred materials include those that impart flavor, sweetness, medicinal benefits and dietary benefits. Furthermore nutrients such as nitrogen, potassium, and phosphorus containing materials are preferred. Many of these materials have been designed into slow dissolving and time released formats. Those experienced in the art will recognize the ease of applying these materials in the current invention.

Those experienced in the art will also understand that both the expanding materials and the optional non-expanding materials may be surface modified with a range of compounds and different binding methods. Examples of preferred surface modification chemicals include chemical agents selected from 3-acryloxypropylotrichlorosilane, 3-acrlyoxypropylotrimethocysilane, Allyltrichlorosilane, allyltrimethoxysilane, allyltriethoxysilane, 3-bromopropylotrichlorosilane, 3-bromopropyl-trimethoxysilane, (p-chloromethyl)phenyltrichlorosilane), (p-chloromethyl)phenyltrimethoxysilane,1-trimethoxysilyl-2-2(p,m-chloromethyl)-phenylethane, chloromethyltrichlorosilane, chloromethyltriethoxysilane, 2-chloroethyltriethoxysilane, 3-chloropropyltrichlorosilane, 3-chloropropyl-trimethoxysilane, 3-glycidoxypropyltrimethoxysilane, 3-iodopropyl trimethoxysilane, 3-isocyanatopropyltriethoxysilane, 2-(diphenylphosphino) ethyltriethoxysilane, vinyltriacetoxysilane,vinyltrichlorosilane, vinyltriethoxysilane, vinyltrimethoxysilane, 3-mercaptopropyltrimethoxysilane, 3-mercaptopropyltriethoxysilane, N-(triethoxysilylpropyl) urea, 3-aminopropyl-triethoxysilane, 3-aminopropyltrimethoxy silane, N-(2-aminoethyl)-3-aminopropyltrimethoxysilane, 2-(carbomethoxy) ethyltrichlorosilane, N-[(3-trimethoxysilyl)propyl]ethylenediamine triacetic acid, trisodium salt, 3-cyanopropyltrichlorosilane, 3-cyanopropyltriethoxysilane, 2-(4-chlorosulfonylphenyl) ethyltrichlorosilane, 2-(4-chlorosulfonylphenyl) ethyltrimethoxysilane, 2-(trimethoxysilyl) ethyl-2-pyridine, N-(3-trimethoxysilylpropyl) pyrrole, N-octadecyldimethyl-1(3-trimethoxysilyl) propyl] ammoniumchloride, N-trimethoxysilylpropyl-n,n,n-trimethyl ammonium chloride, 3-(trimethoxysilyl)

propyldimethyloctadecylammonium chloride silane quaternary amine, chloropropyl trihydroxy silane, polyamines, polyamides, polyalcohols, polysaacharides, polyacrylamides, polyacrylates, humic acids, peptides, proteins, polorganozirconates, polyorganoaluminates, polysiloxanes, polysilanes, polysilazanes, polycarbosilanes, polyborosilanes, zirconium dimethacrulate, zirconium tetramethacrylate, zirconium 2-ethylhexanoate, aluminum butoxides, aluminum diisopropoxide ethylacetoacetate, tetramethyldisiloxanes and derivatives thereof, tristrimethylsilylphosphate and tristrimethylsiloxyboron, polyamines such as poly(DADMAC), poly-DADM, polyamine-poly(DADMAC) blends, polyquartenary amines, inorganic-polyamine blends, and inorganic poly(DADMAC) blends, cationic starch, cationic poly-methylmethacrylates, copolymers of vinylimidazolium methochloride and vinylpyrrolidone, quarternized vinylpyrrolidone/dimethyl-aminoethyl-methacrylate copolymer, polyethyleneimine, or combinations thereof.

Additionally, surface binding methods that provide the capacity of immobilizing genetic material, proteins, peptides, antibodies, and pharmaceutical agents are preferred means of modifying the surfaces of both the expanding and non-expanding materials. Those experienced in the art will recognize that numerous procedures exist for generating stable surface coatings of these materials. Furthermore the ability to immobilize genetic information as well as proteins and peptides facilitates the use of the materials of the invention in sensing and sensor development.

The materials and methods of the invention are unique in the capacity to expand with a range of different fluids that are useful for fluid treatment. Expandable materials may be expanded with synthetic and natural fluids, inorganic, organic, and combinations of both, such as acids, bases, oxidizing agents, reducing agents, precipitating agents, polymerization agents, flocculating agents, surfactants, salts, halogens, peroxides, persulfates, carbonates, amines, polyamines, quaternary amines, medicinal agents, eye care agents, lens care agents, dental care agents, oral care agents, pharmaceutical agents, nutraceuticals, dietary supplements, alcohol or mixture of alcohols, fragrances, odor neutralizing agents, odor masking agents, disinfecting agents, preservatives, biocides, bacteriostats, fungistats, osmostic regulators, sequestering agents, chelating agents, and binders pesticides, insecticides, herbicides, phermones, and animal attractants, cleaning solutions, fatty acids, soaps, and sweetening agents.

Additionally, appropriate combinations of the listed agents with solvent combinations, and sequestering agents facilitates the expanding of the expandable material with an extremely wide range of solution types and ratios. Fluids used to expand the materials of the invention may be delivered to the fluid that is to be treated or retained. Those experienced in the art will recognize the compatibility issues between fluid types and dissolved species carried by the fluids. Further, those experienced in the art will recognize that the nature and identity of the expandable material will vary in the presence of these fluid types and the dissolved species carried by the fluids. Furthermore, those experienced in the art will recognize that the properties of the expandable materials will be modified as the concentrations of fluids and dissolved species they contain vary throughout the course of fluid treatment. Furthermore, those experienced in the art will recognize that physical parameters including temperature and irradiation will effect the materials of this invention.

The materials and methods of the invention are further unique in the capacity to generate fluid treatment compounds from soluble precursors associated with the fluid expanding material, optional nonexpanding materials, or combinations of both. By expanding the fluid expandable material with solutions containing soluble chemical species and subsequently exposing the material to appropriate agents and physical processes, insoluble or reduced solubility materials may be formed. This method of material fabrication allows many materials to be generated in a form that maintains certain aspects of their function. Examples of preferred materials that may be formed in this manner include insoluble minerals such as phosphates, sulfates, sulfides, carbonates, chlorides, bromides, iodides, fluorides, oxides, hydroxides, silicates, cyanides, thiocyanates, arsenates, oxalates, chromates, manganates, reduced metals, and combinations thereof. Further, organic and biological reactions may be used to generate useful fluid treatment agents in and associated with the expandable fluid materials and optional nonexpanding materials. Furthermore, electrochemical, photochemical, and thermally induced reactions may be conducted in the materials of the invention which allows the fabrication of unique materials. Examples include the synthesis of polymers and the reduction of metals.

The materials and methods of the invention are further unique in the capacity to generate agents such as gases and liquids containing reactive agents by contacting the fluid expanded materials with gas, liquid, and solid agents of combinations thereof. This capacity allows safe and controlled reactions to occur. Agents that may be generated with these materials include gases, and liquids and fluids that contain the products of these reactions. Preferred reactions include those that generate gases for disinfection, cleaning, energy production, breathing, and controlling atmospheric components. Likewise preferred applications where liquids and dissolved agents are utilized include medicinal, dental, cleaning, disinfection, and power generation.

The porosity of the composite materials of the invention may be tuned through the choice of expandable and non-expandable materials, fluids, and dissolved or suspended materials. The porosity of the materials may be tailored to allow complete absence of flow through the material through complete passage. Those experienced in the art will understand the contact time, bypass, and backpressure parameters that are associated with these flow dynamics.

The composite materials of the invention are widely applicable to many industries, fluid treatment situations, and for the development of products that serve the needs of consumers, healthcare, industry, and defense related operations. The material of this invention requires no expensive instrumentation or equipment, or significant expertise to fabricate. Expanding and optional non-expanding materials may be mixed, homogenously or heterogeneously in any ratio and composition and may simply be added to a supporting structure of sufficient size and strength to contain the composite. This facilitates the production of many different sizes, shapes, and designs.

The composite materials of the invention allow contaminants to be removed from a fluid, converted to less toxic forms as well as collected and concentrated for further analysis. Materials and devices of the invention are also well suited for the delivery of agents to fluids. The latter capacity allows the materials to be used in fluid treatment for the preparation of beverages, cleaning solutions, eye care solutions, lens care solutions, dental solutions, oral cavity treatment solutions, and agents for further reaction.

The invention has numerous advantages compared to former means of completing many of these fluid treatment tasks. These include the elimination of electrical equipment such as pumps and technical know-how required to correctly dose agents into fluids in a stable and consistent fashion. When the fluid to be used in dosing applications is hazardous incorporation into the expandable materials increases the safety of handling the agent, eliminating the possibility of spills and leaks, and facilitating neutralization and cleanup if a need existed. When solutions are prepared in correct ratios and used to expand the materials of the invention they may be used as concentrates for the production of beverages, or cleaning solutions for fluids, surfaces, chemical toxins, teeth, dental structures, and contact lenses, as well as treatment solutions for eyes, skin, hair and other body parts, with reduced concentrations. Accurate composite material preparation allows accurate solutions to be prepared in a safer and more controlled manner. Additionally, the materials of the invention may be used for sensing and detecting microorganisms in fluid streams. The materials of the invention may also be used for connecting a reservoir to a system for fluid treatment. The fluid expandable material provides a barrier between the fluid requiring treatment and a reservoir that contains a fluid treatment agent. The properties of the composite material control the rate of agent transport between the reservoir and the fluid. The reservoir may contain solid, liquid or gaseous agents. The materials of the invention may also be used to increase the safety of chemical reactions that produce fluid treatment agents such as disinfection gases, by allowing two solid materials (one true solid and one fluid expandable carrier) to be combined instead of a hazardous liquid and a solid.

Those familiar with the art of fluid filtration will understand that the pore size and physical dimensions of the composite purification material may be manipulated for different applications and that variations in these variables will alter flow rates, back-pressure, and the magnitude of chemical and/or microbiological contaminant removal or delivery. Likewise those knowledgeable in the art will recognize that variations in the percentages of each component of the composite purification material will provide variable utility. For example, increasing the percentage of expanding matter in the composite purification material will result in a material having an increased pressure drop and lower flow, while decreasing the percentage of expanding matter will result in a composite purification material having flow rate and pressure drop properties closer to that of granular materials.

In one particular embodiment of the invention, the composite material is formulated to remove contaminants from a gas. Gas phase contaminants may include acid gases formed during combustion processes, dry particulate matter, and aerosols. Many excellent materials and devices may be generated by the materials and methods of the invention. As example, a suitable treatment material may be generated by expanding polyacrylic acid particles with an agent such as an aqueous solution of sodium hydroxide or another hydroxide containing agent, and placing the material in a porous polyethylene container. A suitable example is provided in FIG. 4A. When acid gases such as hydrogen chloride, carbon dioxide, nitrogen oxides, sulfur oxides, and hydrogen cyanide contact the composite media the gases are neutralized and the neutralization products dissolved in the liquid matrix of the composite material. Likewise aerosols of aqueous solutions when contacting the composite media are absorbed into the matrix of the composite material as long as the capacity of the individual particles has not been reached. Particulate matter depending upon size is adsorbed on the surface of the composite material, incorporated into the liquid matrix of the composite material, or combinations thereof. Particulate material is also mechanically removed by interaction with the support structure for the composite material which can be constructed from membrane materials. Sensing an monitoring of hydroxide concentration in the composite can be completed by a number of different methods including colorimetric indicators, and electrochemical sensors.

In another particular embodiment of the invention, the composite material detailed in the previous embodiment is used is used to remove dissolved and particulate contaminants and modify the pH of water to be used for drinking. Drinking water contaminants include dissolved metals and suspended particulate matter. Acidic pH water is corrosive to plumbing systems. When the contaminated low pH water is exposed to the composite media dissolved metal ions such as iron form insoluble hydroxides that may be mechanically removed from the fluid. Additionally these materials adsorb other dissolved contaminants including dissolved metals and organics. Suspended particulate matter is adsorbed on the surface of the composite materials and mechanically removed from the fluid by both the support (container) and the pore size of the composite material. Finally, as the acid water contacts the composite material the water is neutralized, raising the pH to acceptable levels. Sensing an monitoring of hydroxide concentration in the composite can be completed by a number of different methods including colorimetric indicators, and electrochemical sensors.

In another particular embodiment of the invention, the composite material detailed in the previous embodiment is used is used to remove dissolved and particulate contaminants and modify the pH of water to be used for drinking, but is also connected to a reservoir. This reservoir contains a concentrated form of sodium hydroxide. An example of the device is provided in FIG. 1C. Drinking water contaminants include dissolved metals and suspended particulate matter. Acidic pH water is also corrosive to plumbing systems. When the contaminated water is exposed to the composite media dissolved metal ions such as iron form insoluble hydroxides that may be mechanically removed from the fluid. Additionally these materials adsorb other dissolved contaminants including dissolved metals and organics. Suspended particulate matter is not removed from the fluid stream, by the composite media, in this embodiment. Finally, as the acid water contact the composite material the water is neutralized, raising the pH to acceptable levels. The reservoir in this embodiment may be prepared using solid or liquid sodium hydroxide, or other hydroxide generating mechanism, including those based on electrochemical and electrode incorporation. The properties of the fluid being treated, the total area of the composite material as well as other physical and chemical parameters control the movement of treatment agent to the fluid. In this embodiment, there may also be removal of contaminants from the fluid undergoing treatment to the reservoir. This depends upon the nature of the fluid, contaminant, and method of the invention.

Figure 5A:
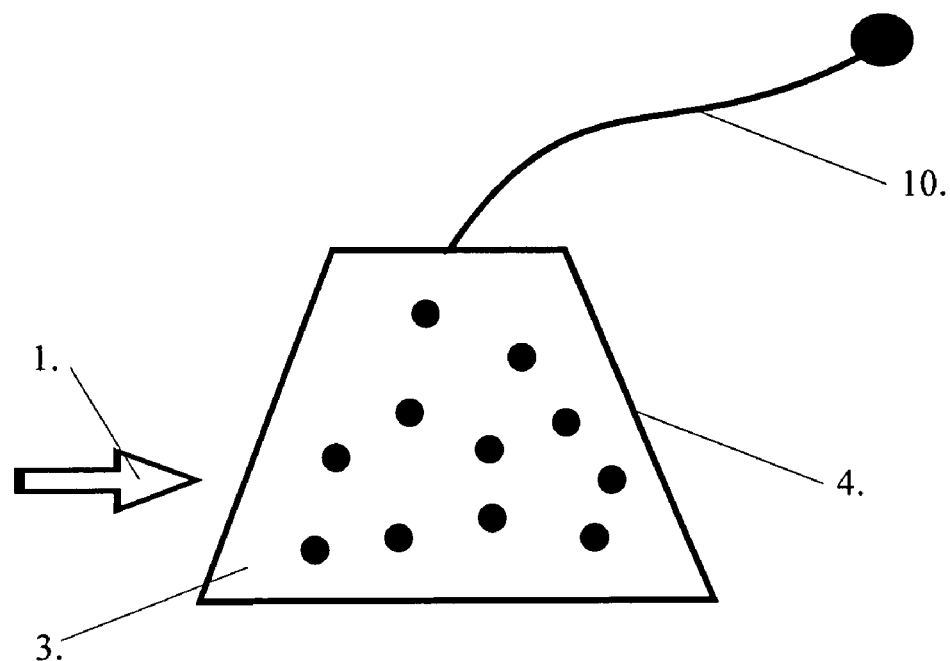
FIG. 5A is a cross-sectional view illustrating a particular embodiment of the invention, namely a porous housing (bag) containing composite material comprising fluid expandable material, expanded with a fluid treatment agent and combined with an optional nonexpanding material and presented in "tea-bag" format that is commonly available for consumer-use in preparing beverages and introducing fragrances into the air. In this format beverages may be prepared based on the contents of the composite material. In some cases this embodiment includes the treatment of fluid contaminants present in the fluid used to prepare the beverage.
Figure 5B:
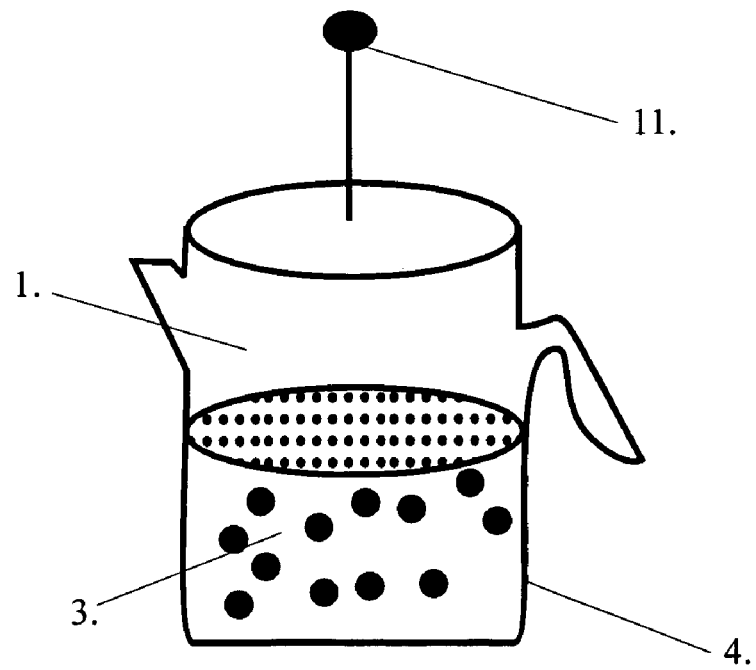
FIG. 5B is a cross-sectional view illustrating a particular embodiment of the invention, namely loose composite materials (fibers, particles) comprising fluid expandable material, expanded with a fluid treatment agent and combined with an optional nonexpanding material and presented in "loose-coffee-maker" format that is commonly available for consumer-use in preparing beverages. In this format beverages may be prepared based on the contents of the composite material. In some cases this embodiment includes the treatment of fluid contaminants present in the fluid used to prepare the beverage.

In another particular embodiment of the invention, the composite material is prepared with a beverage concentrate for the production of a beverage. An aqueous solution containing a high concentration of sweetening agents, natural and artificial flavorings, phosphoric acid, and coloring agents is used to expand polyacrylic acid particles. When these composite materials are exposed to water, in devices as depicted in FIGS. 5A and 5B, the concentrated beverage agents contained in the composite are released, generating a beverage. In this embodiment, containment of the composite material is provided by a porous sheet (FIG. 5A) and by a porous mesh screen (FIG. 5B). In this embodiment, dissolved and suspended contaminants may also be removed by interacting with the composite material as well as the support system provided for containing and/or isolating the composite material. As example, water hardness ions and dissolved metal species may adsorb to the surface of the polyacrylic acid and to the support system for the device used to contain the composite material. This embodiment may also be extended by incorporating a reservoir with the beverage concentrate. Likewise, this embodiment demonstrates the ability to deliver other agents including, bacteriostatic and disinfection agents, medicinal agents, cleaning agents, eye care solutions, lens cleaning solutions, dental care and oral care solutions, solutions for neutralizing chemical toxins, and health and dietary agents.

In another particular embodiment of the invention, a composite material is formed by generating insoluble fluid treatment compounds using soluble precursors contained by the expandable matter. Many different insoluble fluid treatment compounds may be generated through the method of this invention. As a specific example, a water soluble sodium phosphate compound may be used to expand polyacrylic-polyacrylamide particles. When these particles are exposed to an aqueous solution of calcium chloride, calcium phosphate is generated. The composite material may be used directly for fluid treatment. An additional example includes the expanding of the same polymer particles with an aqueous solution of aluminum sulfate. When these particles are exposed to solutions with elevated pH, aluminum hydroxides are formed and the material may be directly used in fluid treatment.

In another particular embodiment of the invention, the composite material may be used to generate agents for fluid treatment such as gases. Many different gases are commonly injected into fluids for different reasons. Carbon dioxide is injected for beverage production, chlorine dioxide and chlorine are injected for disinfection purposes, oxides of nitrogen are injected for medicinal purposes, and oxygen and nitrogen ratios are varied for respiratory purposes. Gases may also be generated for power production and fuel cell operation. Gases are often generated by the reaction of soluble chemicals, electrochemical reactions, or through direct injection of the stored gas. In this embodiment gases are generated either through chemical reaction between an agent contained by the composite material and a second reagent in solid, liquid, gaseous form or by contacting an electrode with the composite media for the same purpose. Those experienced in the art will understand that electrode function may affect the expansion characteristics of the composite material. As example, a polyacrylic acid may be expanded with an aqueous solution of hydrogen chloride. Exposure of this materials to sodium bicarbonate generates carbon dioxide. Those experienced in the art will recognize that many different acids may be used for similar purpose. In an additional example that illustrates this embodiment an aqueous solution of ammonium chloride is used to expand polyacrylic acid particles. Exposure of this material to solid sodium hydroxide pellets, generates ammonia gas. This gas may be used for cleaning operations as well as fuel cell operation. In these examples the water and soluble reaction products generated may also be contained by the composite material, avoiding the leaking of liquids from the device used to conduct the fluid treatment operation.

In another particular embodiment of the invention, a composite material is fabricated which is used to prepare cleaning solutions. Cleaning solutions often contain surfactants and acidic or caustic agents that are irritating to the user. For many applications these solutions are usually sold in concentrated form. The mixing and subsequent use of the cleaning fluids may pose a hazard even when prepared correctly. In this embodiment concentrated cleaning solutions are used to expand polyacrylic-polyacrylamide particles. When this composite material is exposed to water in a device as depicted, in FIGS. 1A, 1B, 1C, and 1D, a cleaning solution ready for direct use is generated. These materials and devices may safely store and allow application of the hazardous solutions. These devices allow incorporation into mechanical systems such as sprayers.

In another embodiment of the invention, the composite material is constructed to treat hydrocarbon fuels that are contaminated with water and dissolved and suspended chemical and biological agents. Composites may be prepared to remove the water and associated contaminants and if needed simultaneously deliver biocidial agents.

In another embodiment of the invention, the composite material is constructed to withstand sterilization. Sterilization processes include thermal processes, such as steam sterilization or other processes wherein the composite purification material is exposed to elevated temperatures or pressures or both, resistive heating, radiation sterilization wherein the composite purification material is exposed to elevated radiation levels, including processes using ultraviolet, infrared, microwave, and ionizing radiation, and chemical sterilization, wherein the composite purification material is exposed to elevated levels of oxidants or reductants or other chemical species, and which is performed with chemicals such as halogens, reactive oxygen species, formaldehyde, surfactants, metals and gases such as ethylene oxide, methyl bromide, beta-propiolactone, and propylene oxide. Additionally, sterilization may be accomplished with electrochemical methods by direct oxidation or reduction with microbiological components or indirectly through the electrochemical generation of oxidative or reductive chemical species. Combinations of these processes are also used on a routine basis. It should also be understood that sterilization processes may be used on a continuous or sporadic basis while the composite material is in use.

In another particular embodiment of the invention, a composite material is fabricated for the sensing of microorganisms. Here, polyacrylic acid polyacrylamide particles are expanded with a nutrient media that supports growth of bacteria. When the composite material is exposed to an aerosol containing bacteria the bacteria are adsorbed to the particle surface. The nutrient solution contained by the particle allows propagation of the organisms, as well as sensing, identification, and quantitation of the biological agents. Those experienced the art will recognize that indicator agents may be used in the nutrient media or that the nutrient media may be replaced with a detection media that allows many different types of genetic screening to be completed. Those experienced in the art will also recognize that the surface properties of the composite material may be modified for specific selection of different organisms as well as the stability of the interaction of the organisms on the surface. Those experienced in the art will also recognize that other particle types can simultaneously be collected and that the use of electrical charging of particles through a variety of mechanisms can enhance the collection efficiency of devices incorporating the materials of the invention.

In another particular embodiment of the invention, a composite material is fabricated for the treatment of chemical weapons such as nerve agents. Here, polyacrylic acid polyacrylamide particles are expanded with a solution that collects, neutralizes, and degrades chemical agents and toxins. When the composite material is exposed to the chemical agent chemical reactions which reduce the toxicity of the chemical agents occur. Many of these reactions are exothermic and thus provide a basis for sensing and monitoring the presence of the agents and their degradation. Monitoring these interactions can yield devices which provide information on chemical agent presence as well as providing an indicator for device "end of life" or remaining functional capacity.

In another particular embodiment of the invention, a composite material is fabricated for the treatment of ground water in subsurface locations. Here polyacrylic acid-polyacrylamide particles are expanded with agents that react with contaminants in a fluid plume. These particles may be mixed with minerals such as apatites and with metals such as zero-valent-iron. The composite material may also be linked to a reservoir that contains additional agents for replenishing the composite material. The advantages to the material and devices of this embodiment include the ability to deliver chemical agents in a spatially controlled and timed manner.

In general, the invention comprises a method and a means for fabricating materials and devices for the treatment of fluid, and more specifically for the removal and conversion of contaminants, for the delivery of agents, and for sensing and detection purposes. Fluids of particular interest and importance include drinking water, beverage production, cleaning solution preparation, and breathing air. Agent generation of particular interest includes gases such as oxygen, chlorine dioxide, ammonia, and carbon dioxide. Contaminants that need to be removed from drinking water include, metals, microorganisms, pesticides, and the byproducts of the disinfection process. Agents that need to be delivered to beverages include flavorings, sweeteners, colorants, gases, and nutritional and medicinal agents.

A typical specific embodiment of an apparatus containing the composite material of the invention that incorporates a porous composite material is now described. A removable housing is mated with a cap, the cap having an inflow orifice and an outflow orifice. A water or air supply conduit is joined to the inflow orifice to deliver non-treated water or air into the device, and a water or air discharge conduit is joined to the outflow orifice to conduct treated water or air from the device. Water or air passes into the housing and the pressure of the water or air flow forces it through the porous composite material, that is formed in the shape of hollow cylinder with an axial bore, the treated water or air passing into the axial bore that connects to the outflow orifice. It is to be understood that other configurations where water or air is caused to pass through a porous composite material (which may have different geometrical shapes and/or different flow properties) are contemplated to be within the scope of the invention. The composite material is formed by placing both expanding and optional non-expanding media between two capped porous supports of which the outer support limits the outer diameter and the inner support is the central bore. Both supports are chosen to have a pore size smaller than the particles used. In this specific embodiment the pore size of the supports is less than 300 microns and the support composition is polyethylene.

Multiple embodiments where the composite purification material of the invention is used in the form of a sheet, fiber, film, web, or with independent particles moving through a fluid, are envisioned. A composite material used in connection with normal flow-through geometries has the fluid being treated by passage through the sheet, fiber, film, web, particle or combinations thereof. Alternatively a composite purification material may be used in connection with cross-flow filtration. Embodiments where the particles are loosely held or introduced into a stream by injection, dropping, or other physical mechanisms as well as magnetic and electrical field control mechanisms are possible. Collection of the injected particles allows identification of contaminant level changes over periods of time. Likewise, movement of long fibers allows temporal information to be obtained.

With reference to the drawings, the invention and a mode of practicing it will now be described with regard to several particular embodiments, which depict use of the composite materials of the invention and devices incorporating materials of the invention.

FIG. 1A illustrates a typical specific embodiment of a cross flow fluid treatment apparatus containing the composite material of the invention, which incorporates a porous block material that allows limited passage of fluid through the composite material. A removable housing 4 houses the composite material 3 and is situated between fluid conduit 1 (inflow) and treated fluid conduit 6. Fluid conduit 2 indicates outflow for fluid conduit 1.

Figure 1B:
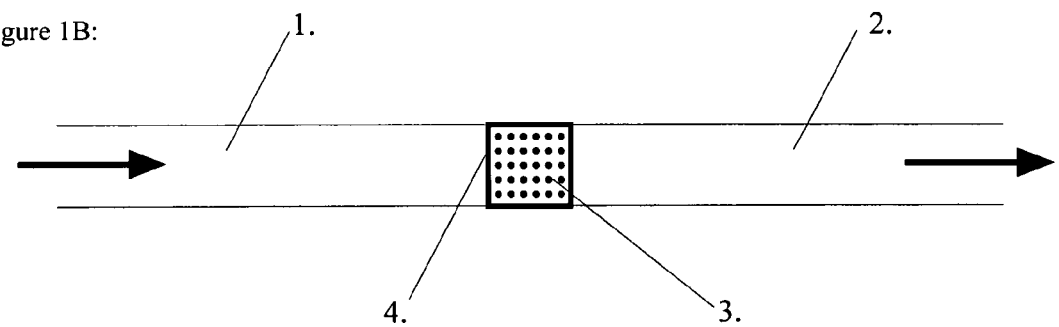
FIG. 1B is a cross-sectional view illustrating a particular embodiment of the invention, namely a porous support (two-sides) containing composite material comprising fluid expandable material, expanded with a fluid treatment agent and combined with an optional nonexpanding material. An appropriate housing is positioned in a flow through geometry.

FIG. 1B illustrates a typical specific embodiment of a fluid treatment apparatus containing the composite material of the invention, that incorporates a porous block material that allows passage of fluid through the composite material. A removable housing 4 houses the composite material 3 and is situated between fluid conduit 1 (inflow) and treated fluid conduit 2.

Figure 1C:
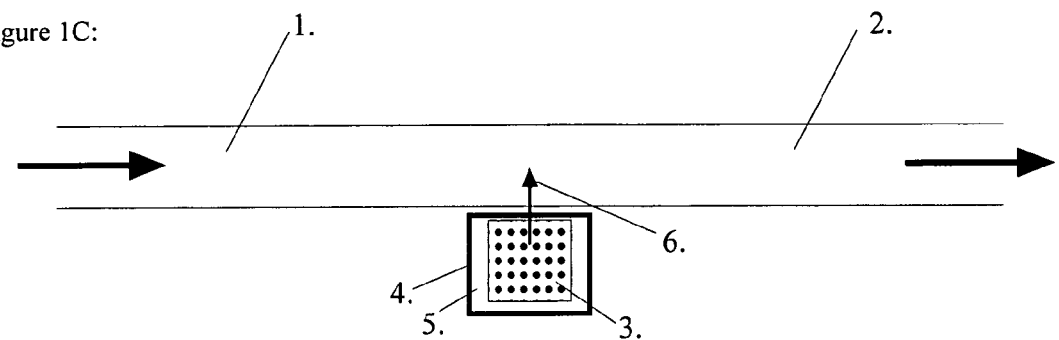
FIG. 1C is a cross-sectional view illustrating a particular embodiment of the invention, namely a porous support (two-sides) containing composite material comprising fluid expandable material, expanded with a fluid treatment agent and combined with an optional fluid nonexpanding material. An appropriate housing is positioned in a cross-flow filtration geometry or a flow-through geometry and connected to a reservoir that contains a fluid treatment agent.

FIG. 1C illustrates a typical specific embodiment of a cross-flow or flow-through fluid treatment apparatus containing the composite material of the invention, that incorporates a porous block material that allows limited passage of fluid through the composite material, and a reservoir. A removable housing 4 houses the composite material 3 and is situated between fluid conduit 1 (inflow) and treated fluid conduit 6. Fluid conduit 2 indicates outflow for fluid conduit 1. Removable housing 4 and composite material 3 are connected to a reservoir 5.

Figure 1D:
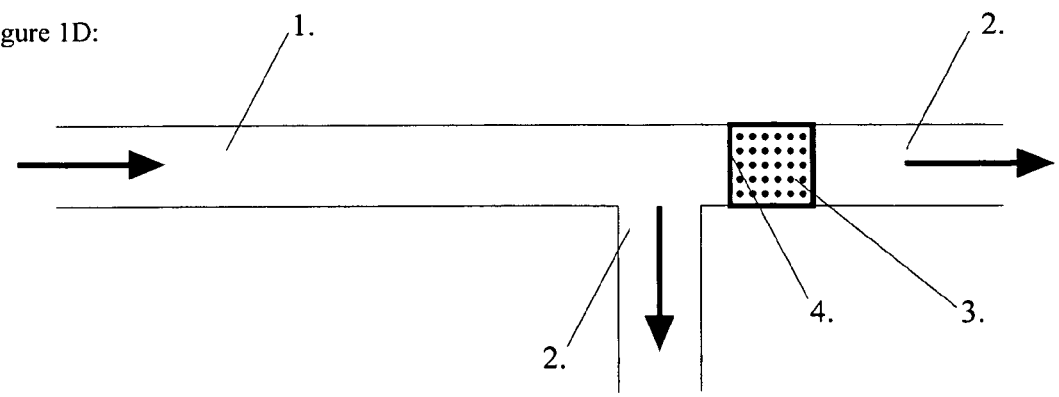
FIG. 1D is a cross-sectional view illustrating a particular embodiment of the invention, namely a porous support (two sides) containing composite material comprising fluid expandable material, expanded with a fluid treatment agent and combined with an optional nonexpanding material. An appropriate housing is positioned in a geometry that may control fluid flow based on porosity and changing porosity of the composite material.

FIG. 1D illustrates a typical specific embodiment of a fluid treatment apparatus containing the composite material of the invention, that incorporates a porous block material that allows controlled passage of fluid through the composite material as well as directing fluid flow. A removable housing 4 houses the composite material 3 and is situated between fluid conduit 1 (inflow) and treated fluid conduit 2. Two different fluid conduit 2s are depicted, one where fluid is translated through the composite material and one where fluid only has a limited surface interaction with the composite material. Removable housing 4 and composite material 3 could be connected to a reservoir as indicated in FIG. 1C, if desired.

Figure 2A:
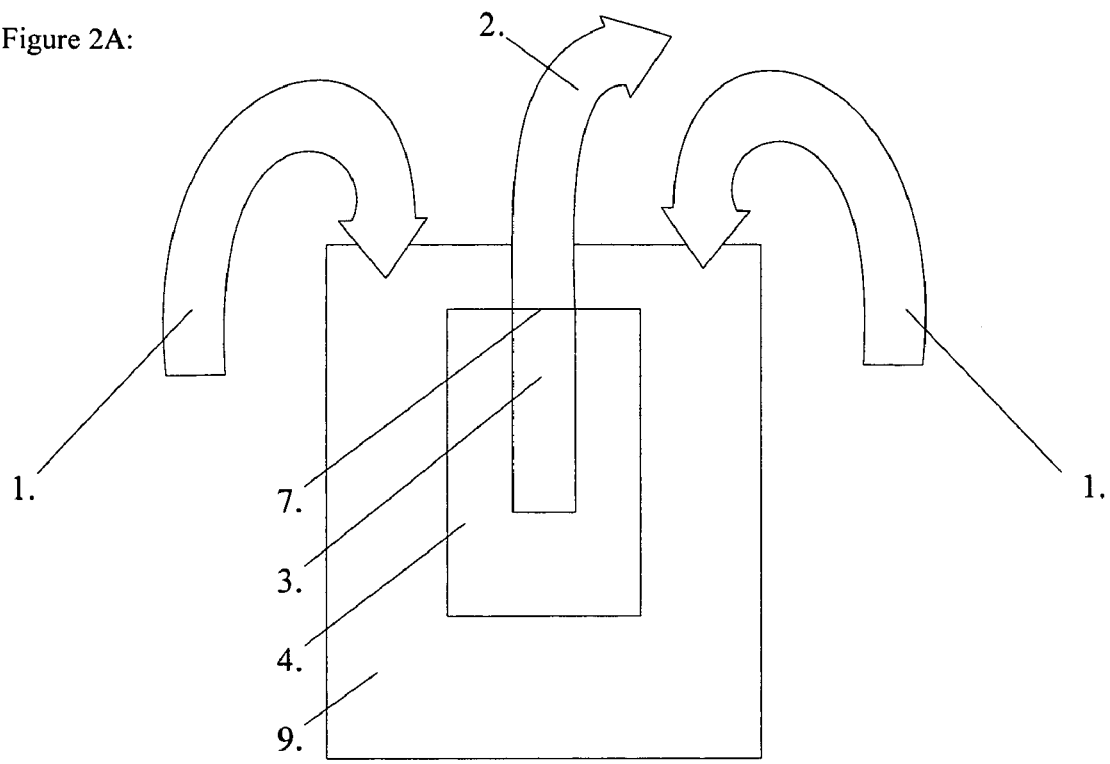
FIGS. 2A and 2B are cross-sectional views illustrating particular embodiments of the invention, namely a porous support (cartridge) containing composite material comprising fluid expandable material, expanded with a fluid treatment agent and combined with an optional nonexpanding material. The cartridge containing the composite material contains a central bore that allows radial flow through the material of the invention and out of the cartridge housing.

FIG. 2A illustrates a typical specific embodiment of a fluid treatment apparatus containing the composite material of the invention, that incorporates a porous block material that allows passage of fluid through the composite material. A removable housing 4 houses the composite material 3 that has a central bore 7 for fluid 2 to exit (outflow). Fluid inflow 1 is through a cap on container 9 that houses removal housing 4. This figure illustrates a standard radial flow device.

Figure 2B:
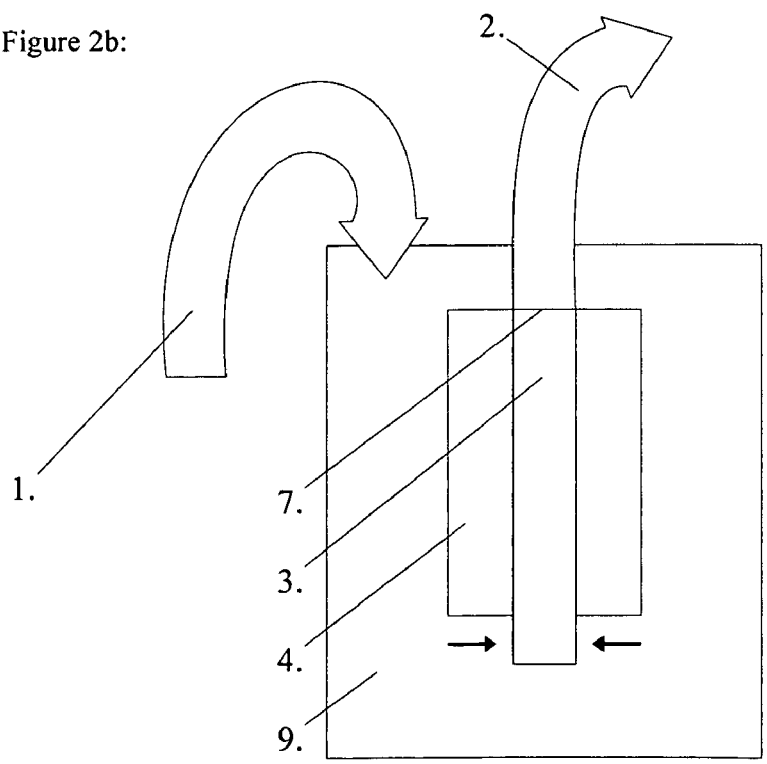

FIG. 2B illustrates a typical specific embodiment of a fluid treatment apparatus containing the composite material of the invention, that incorporates a porous block material that allows passage of fluid through the composite material. A removable housing 4 houses the composite material 3 that has a central bore 7 for fluid 2 to exit (outflow). Fluid inflow 1 is through a cap on container 9 that houses removal housing 4. This figure illustrates a standard radial flow device. In this device the central bore 7 extends past the composite material housing 4 and reduces interaction with fluid inflow 1, and is one method of increasing flow and reducing contact with composite material 3.

Figure 3A:
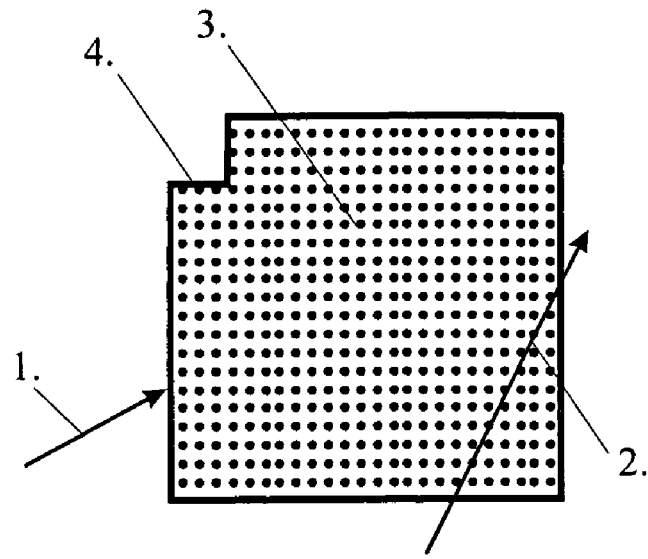
FIGS. 3A and 3B are cross-sectional views illustrating particular embodiments of the invention, namely a porous support (two-sides) containing composite material comprising fluid expandable material, expanded with a fluid treatment agent and combined with an optional nonexpanding material and presented in a planar format that is typical of air filters. The planar format is a flow through design that allows many different thicknesses to be used.

FIG. 3A illustrates an embodiment where the composite material of the invention is used in the form of a sheet or film. Composite material 3 housing 4 is used to treat influent fluid 1. Two effluent fluids 2 exist one that demonstrates a cross flow design and one that demonstrates a flow through design.

Figure 3B:
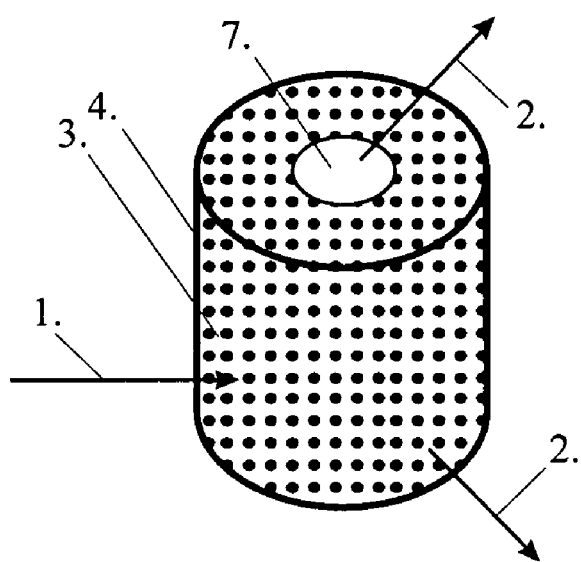

FIG. 3B illustrates an embodiment where the composite material of the invention is used in the form of a sheet or film and wrapped around a central bore 7. Composite material 3 and housing 4 is used to treat influent fluid 1. Two effluent fluids 2 exist one that demonstrates a cross flow design and one that demonstrates a flow through design.

Figure 4A:
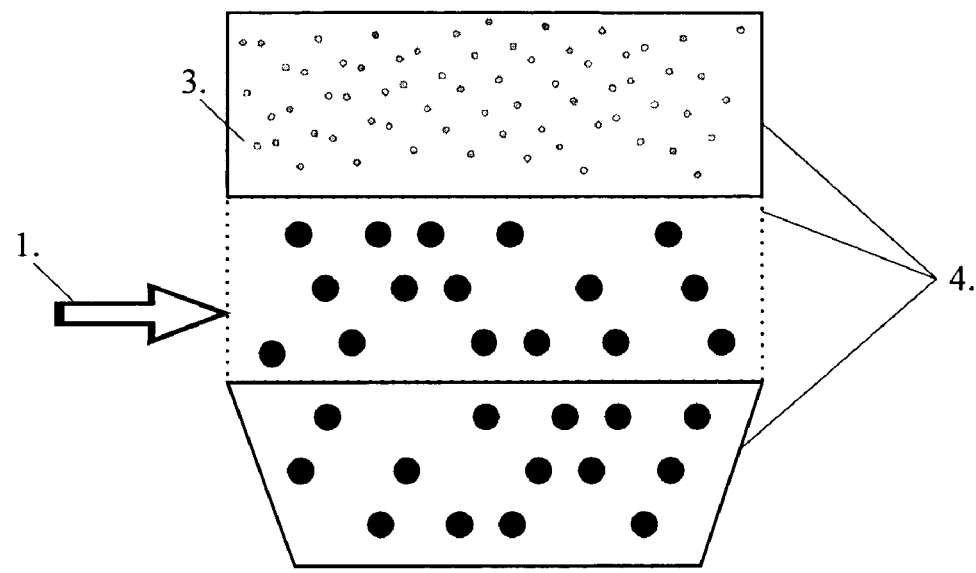
FIGS. 4A and 4B are cross-sectional views illustrating particular embodiments of the invention, namely a porous drop zone (four sides), a reservoir containing composite material comprising fluid expandable material, expanded with a fluid treatment agent, and including a collection basin. In this embodiment expanded composite particles move through the drop zone by the force of gravity. While moving through the zone the particles collect contaminants that are analyzed in the collection basin or are removed and analyzed.

FIG. 4A illustrates a typical specific embodiment of a fluid contaminant sensing apparatus (planar) containing the composite material of the invention, which individual particles of the material that pass through the fluid to be sensed. A housing 4 contains both a reservoir and a receptacle for composite material particles 3. Fluid flow 1 interacts with particles falling in housing 4. Particles 3 may be guided by a porous mesh (no shown for clarity).

Figure 4B:
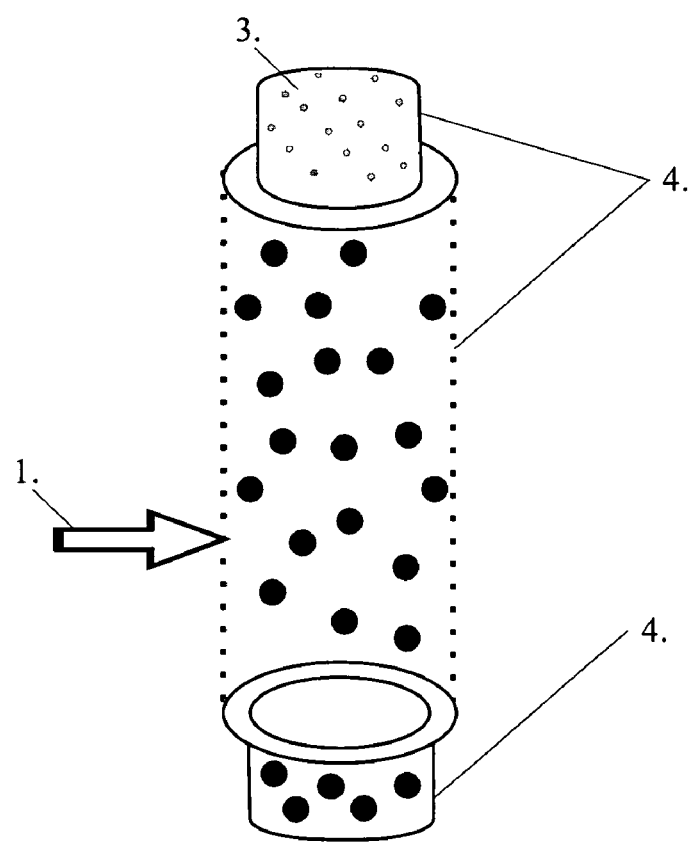

FIG. 4B illustrates a typical specific embodiment of a fluid contaminant sensing apparatus (cylindrical) containing the composite material of the invention, which individual particles of the material that pass through the fluid to be sensed. A housing 4 contains both a reservoir and a receptacle for composite material particles 3. Fluid flow 1 interacts with particles falling in housing 4. Particles 3 may be guided by a porous mesh (not shown for clarity).

FIG. 5A illustrates a typical specific embodiment of a fluid treatment apparatus containing the composite material of the invention, which individual particles contained in a disposable single use package. A housing 4 contains composite material particles 3. When housing 4 and material 3 is placed in contact with fluid 1 the contents of particles 3 are released into fluid 1. This "tea-bag" example is illustrated with a string 10 for positioning.

FIG. 5B illustrates a typical specific embodiment of a fluid treatment apparatus containing the composite material of the invention, which individual particles are placed loose into a housing 4. Fluid 1 is placed in with particles 3 and plunger 11 that holds a porous material is used to confine particles 3 when liquid is poured from housing 4. A housing 4 contains composite material particles 3. When particulate material 3 is placed in contact with fluid 1 the contents of particles 3 are released into fluid 1. This "loose-coffee-maker" example is illustrated in a common configuration.

The following examples exemplify the type of composite materials that may be generated under the methods of the invention.

EXAMPLES

Example 1

A beverage syrup containing phosphoric acid, coloring agents, sweeteners, and flavoring agents, was absorbed in an expandable polyacrylic acid particle. The syrup was then released when exposed to water.

Example 2

An iodide solution was absorbed in an expandable polyacrylic acid particle. A purple colored composite was generated. The color was removed when a solution containing ascorbic acid was exposed to the composite.

Example 3

The following acids were absorbed into an expandable polyacrylic acid particle: hydrochloric, phosphoric, sulfuric, hydrofluoric, citric, and boric. The composites were stable for many days.

Example 4

The following bases were absorbed into an expandable polyacrylic acid and polyacrylamide-polyacrylic acid particles: sodium hydroxide, ammonium hydroxide, and potassium hydroxide. The composites were stable for many days.

Example 5

The following salt solutions were absorbed into an expandable polyacrylic acid and polyacrylamide-polyacrylic acid particles: sodium chloride, sodium bicarbonate, silver nitrate, and calcium chloride. The composites were stable for many days.

Example 6

Nanometer size particles of reduced silver were generated with expandable polyacrylic acid and polyacrylamide-polyacrylic acid particles using silver nitrate and irradiation. Composite color was tunable based upon parameters used and included blues and reds. When the composite material was exposed to tap water silver chloride was formed. After a period of time silver ion was generated.

Example 7

The following metal ion solutions were absorbed into an expandable polyacrylic acid-polyacrylamide particle, copper, iron, lanthanum, and aluminum. The composites could be dried and re-expanded upon exposure to fluid.

Example 8

A mixed ionic flocculating solution was absorbed into an expandable polyacrylic acid-polyacrylamide particle. The flocculating agent was released upon exposure to fluid.

Example 9

A potassium permanganate solution was absorbed into an expandable polyacrylic acid-polyacrylamide particle. Manganese oxide(s) was formed in the process. Dried composite particles expanded when exposed to fluid. When composite particles were exposed to hydrogen peroxide, oxygen gas was generated.

Example 10

A hydrochloric acid solution was absorbed into an expandable polyacrylic acid-polyacrylamide particle and when exposed to solid sodium bicarbonate, carbon dioxide evolved.

Example 11

A hydrochloric acid solution was absorbed into an expandable polyacrylic acid-polyacrylamide particle and when exposed to solid sodium chlorite, chlorine dioxide evolved.

Example 12

A sodium thiosulfate solution was absorbed into an expandable polyacrylic acid particle. When the composite was exposed to a solution containing hypochlorous acid the acid was neutralized.

Example 13

An alcoholic solution containing a mixture of vitamins was absorbed into an expandable polyacrylic acid particle. The composite was stable for many days.

Example 14

A concentrated solution of monoethanolamine was absorbed into an expandable polyacrylic acid particle. The composite was stable for many days.

Example 15

A concentrated solution of octenol, an insect attractant was absorbed into an expandable polyacrylic acid particle. The composite was stable for many days.

Example 16

A solution containing cyclodextrins and odor neutralizing compounds was absorbed into an expandable polyacrylic acid particle. The composite was stable for many days.

Example 17

A solution containing sodium bicarbonate absorbed into an expandable polyacrylic acid particle, and when exposed to calcium ion calcium carbonate formed.

Example 18

Tap water was absorbed into an expandable polyacrylic acid-polyacrylamide particle and frozen. Upon warming, the composite returned to a hydrated form.

Example 19

The following oxidizers were absorbed into an expandable polyacrylic acid and polyacrylamide-polyacrylic acid particles: hypochlorous acid, sodium monopersulfate, stabilized chlorine, and hydrogen peroxide. The stability of the composite was determined by oxidizer concentration and environmental parameters.

Example 20

A solution containing a dissolved aspirin tablet was absorbed into an expandable polyacrylic acid particle. The composite was stable for many days.

Example 21

A solution containing ethylenediaminetetraacetic acid (EDTA) was absorbed into an expandable polyacrylic acid particle. The composite was stable for many days.

Example 22

An eye care solution containing saline, boric acid, and borate, as well as a disinfectant was absorbed into an expandable polyacrylic acid particle. The composite was stable for many days.

Example 23

A dental/oral care solution containing alcohol, flavoring, coloring, and plaque treatment agent, was absorbed into an expandable polyacrylic acid particle. The composite was stable for many days.

Example 24

A biodegradable cleaning solution containing polyethylene glycol, ethers, modified sulfonates, and coloring agents, was absorbed in concentrated form into polyacrylic acid particles. The composite was stable for many days.

As described above, the composite material and mixtures of different composite materials of the invention are extremely useful in the area of containing or storing chemical species for reaction of or delivery into fluids. Composites when exposed to fluids may release their contents under controlled situations, may generate gases, may interact with radiation, may react with species in the fluid stream and in many cases may be used in a reversible manner or recharged for further use. The composites are useful in both gas filtration and liquid purification, particularly in the area of purifying breathable air and drinking water. Because of the high efficiency and simplicity with which the composite materials of the present invention may function the materials of the invention are useful in many industries and consumer products, and appliances. Specifically, the products may be used in drinking water applications, passive air treatment application, forced air applications, humidification and dehumidification systems, water used for recreational purposes, such as water used in swimming pools, hot tubs, and spas. The materials may be used in appliances such as refrigerators, fluid coolers/chillers, water fountains, and beverage dispensing systems. They may be used in cleaning systems that use automatic washers, manual washers, high pressure sprayers, and the like.

As the result of the ability of the material of the invention to efficiently collect, immobilize, and provide a platform for microorganism and other biological agents sensing, it has numerous applications in both civilian and military defense applications. Further, the material of the invention can house reactive solutions which can collect, isolate, detect, neutralize, and degrade chemical toxins.

The pharmaceutical and medical fields may use materials of the invention to treat blood, surgical fluids, wounds, and provide protective devices for both patient and attendant. The eye care, lens care, dental care, and oral care fields may utilize the materials of the invention The material may also be used in hospital, industrial areas, or enclosed areas requiring highly purified air having extremely low content of microorganisms, e.g., in intensive care wards, operating theaters, and clean rooms used for the therapy of immunosuppressed patients, or in industrial clean rooms used for manufacturing electronic and semiconductor equipment.

The material of the invention has multiple uses in fermentation applications and cell culture, where it may be used to remove microorganisms from aqueous fluids, such as fermentation broths or process fluids, allowing these fluids to be used more efficiently and recycled, e.g., without cross-contamination of microbial strains. In addition, because the material is so efficient at removing microorganisms and at retaining them once removed, it may be used as an immobilization medium for enzymatic and other processing requiring the use of microorganisms. A seeding solution containing the desired microorganisms is first forced through the material of the invention, and then substrate solutions, e.g., containing proteins or other materials serving as enzymatic substrates, are passed through the seeded material. As these substrate solutions pass through the material, the substrates dissolved or suspended therein come into contact with the immobilized microorganisms, and more importantly, with the enzymes produced by those microorganisms, that may then catalyze reaction of the substrate molecules. The reaction products may then be eluted from the material by washing with another aqueous solution.

The material of the invention has numerous other industrial uses, e.g., treating water used in cooling systems. Cooling water often passes through towers, ponds, or other process equipment where contaminants may come into contact with the fluid.

Similarly, breathable air is often recycled in transportation systems, either to reduce costs (as with commercial airliners) or because a limited supply is available (as with submarines and spacecraft). Efficient removal of contaminants permits this air to be recycled more safely. In addition, the material of the invention may be used to increase indoor air quality in homes, buildings, enclosed areas, and protective shelters, in conjunction with the air circulation and conditioning systems already in use therein. The composite material of the invention may also be used to purify other types of gases, such as anesthetic gases used in surgery or dentistry (e.g., nitrous oxide), gases used in the carbonated beverage industry (e.g., carbon dioxide), gases used to purge process equipment (e.g., nitrogen, carbon dioxide, argon), and/or to remove particles from surfaces, etc.

The composite materials of the invention may be used to generate catalytic devices based upon chemicals such as metals, metal oxides, and biochemical agents such as enzymes. These devices may be used to treat or remediate emission gases such as those generated by the chemical, mining, power, and manufacturing industries as well as those generated from consumer products such as those powered with combustion engines. They may be used to generate gases for specific applications such as oxygen for respiration.

In each of these applications, the method of using the material of the invention is relatively simple and should be apparent to those of skill in the filtration art. The fluid to be treated is simply conducted to one side of the composite material of the invention, typically disposed in some form of housing, and forced through the material as the result of a pressure drop across the composite purification material, or conducted across the surface. Treated fluid is then conducted away from the "exit" side of the material and further processed or used.

The invention having been thus described by reference to certain of its specific embodiments, it will be apparent to those of skill in the art that many variations and modifications of these embodiments may be made within the spirit of the invention, that are intended to come within the scope of the appended claims and equivalents thereto.

What is claimed is:

1. An assembly comprising: (i) a reservoir and (ii) a composite material comprising
   a fluid expandable material; and
   an agent that modifies the properties of said expandable material,
   wherein said composite material is in contact with the reservoir containing a first chemical or biological agent, and a composite material is disposed between the reservoir and a fluid in need of treatment, and
   wherein the composite material regulates contact between said fluid and said first chemical or biological agent, serving as a conduit for said fluid to pass through said composite material into the reservoir or for said first chemical or biological agent to pass from the reservoir through said composite material into said fluid.

2. The assembly of claim 1, further containing material that does not expand in the presence of fluid.

3. The assembly of claim 2, wherein the non-expanding material is insoluble in the fluid and is selected from synthetic polymers, naturally occurring ion exchange materials, naturally occurring polymers, minerals, activated carbons, and metals.

4. The assembly of claim 2, wherein the non-expanding material is soluble in the fluid and is selected from synthetic polymers, naturally occurring ion exchange materials, naturally occurring polymers, minerals, activated carbons, and metals.

5. The assembly of claim 2, wherein the non-expandable material is in the form of a particle, fiber, block, sheet, web, or combinations thereof.

6. The assembly of claim 2, wherein the non-expanding material can absorb fluid.

7. The assembly of claim 2, wherein the non-expanding material is surface modified.

8. The assembly of claim 1, wherein the composite material is in a form where the presence of the first chemical or biological agent alters the properties of the expandable material.

9. The assembly of claim 1, wherein the composite material is in a form where the release or reaction of the first chemical or biological agent alters the properties of the expandable material.

10. The assembly of claim 1, wherein the composite material is in a form that removes a second chemical or biological agent from the fluid.

11. The assembly of claim 1, wherein the composite material is in a form that both removes a second chemical or biological agent from the fluid and releases the first chemical or biological agent into the fluid.

12. The assembly of claim 1, wherein the expandable material is obtained from synthetic or naturally occurring organic molecules, or a combination thereof.

13. The assembly of claim 1, wherein the expandable material is obtained from synthetic or naturally occurring inorganic molecules, or a combination thereof.

14. The assembly of claim 1, wherein the composite material contains a combination of expandable material obtained from synthetic or naturally occurring inorganic and organic molecules.

15. The assembly of claim 1, wherein the composite material contains an expandable material which is surface modified.

16. The assembly of claim 1, wherein the expandable material is in the form of a particle, fiber, block, sheet, web, or combinations thereof.

17. The assembly of claim 1, wherein the composite material is contained or associated with a porous support.

18. The assembly of claim 17, wherein the composite material and the support are associated with a housing that provides contact with the fluid.

19. The assembly of claim 18, wherein the composite material, the support, and the housing are further associated with a physical system which provides fluid contact.

20. The assembly of claim 19, wherein the physical system is flexible.

21. The assembly of claim 19, wherein the physical system includes cyclones and vortex generators.

22. The assembly of claim 1, wherein the agent that modifies the properties of said expandable material is selected from synthetic organic molecules, synthetic inorganic molecules, naturally occurring organic molecules, naturally occurring inorganic molecules, metals, semimetals, and combinations thereof.

23. The assembly of claim 22, wherein the agent that modifies the properties of said expandable material is selected from acids, bases, oxidizing agents, reducing agents, precipitating agents, polymerization agents, flocculating agents, surfactants, salts, and combinations thereof.

24. The assembly of claim 22, wherein the agent that modifies the properties of said expandable material is selected from amines, polyamines, quaternary amines, and combinations thereof.

25. The assembly of claim 22, wherein the agent that modifies the properties of said expandable material is selected from medicinal agents, pharmaceutical agents, nutraceuticals, dietary supplements, and combinations thereof.

26. The assembly of claim 22, wherein the agent that modifies the properties of said expandable material comprises an alcohol or a mixture of alcohols.

27. The assembly of claim 22, wherein the agent that modifies the properties of said expandable material comprises an insoluble compound which is formed by the reaction with a fluid containing a soluble compound or element contained by the expandable material.

28. The assembly of claim 22, wherein the agent that modifies the properties of said expandable material comprises an insoluble compound which is formed through irradiation, temperature change, or a combination thereof.

29. The assembly of claim 22, wherein the agent that modifies the properties of said expandable material is selected from sequestering agents, chelating agents, and binders.

30. The assembly of claim 22, wherein the agent that modifies the properties of said expandable material comprises a precipitated compound selected from the group consisting of phosphates, sulfates, sulfides, carbonates, chlorides, bromides, iodides, fluorides, oxides, hydroxides, silicates, cyanides, thiocyanates, arsenates, oxalates, chromates, manganates, and combinations thereof.

31. The assembly of claim 1, wherein the composite material contains a biological agent selected from synthetic biological molecules, naturally occurring biological molecules, microorganisms, and combinations thereof.

32. The assembly of claim 1, wherein the composite material contains a biological agent selected from both (i) a biological agent selected from the group consisting of synthetic biological molecules, naturally occurring biological molecules, microorganisms, and combinations thereof, and (ii) a chemical agent selected from the group consisting of synthetic organic molecules, synthetic inorganic molecules, naturally occurring organic molecules, naturally occurring inorganic molecules, metals, semimetals, and combinations thereof.

33. The assembly of claim 1, wherein the composite material is in contact with an electronic device selected from electrodes, heating elements, radiation sources, sensors, communicators, and combinations thereof.

34. The assembly of claim 1, wherein the composite material contains a media that supports a cellular function selected from respiration, metabolism, reproduction, defense, growth, and combinations thereof.

35. The assembly of claim 1, wherein the first chemical or biological agent is in a solid form, a liquid form, or a combination thereof.

36. The assembly of claim 1, wherein the first chemical or biological agent is biodegradable.

37. The assembly of claim 1 wherein the composite material is sized for individual use.

38. The assembly of claim 1 wherein the composite material can be sterilized.

39. The assembly of claim 1, wherein the composite material is useful as a particle filtration device.

40. The assembly of claim 1, wherein the composite material is in a form useful for processing aerosols.

41. The assembly of claim 1, wherein the composite material comprises a sponge or foam material.

42. The assembly of claim 1, wherein the first chemical or biological agent is in a gaseous form, alone or in combination with a solid or liquid form thereof.

43. The assembly of claim 1, wherein the fluid expandable material comprises a polyacrylic acid.

44. The assembly of claim 43, wherein the agent that modifies said expandable material comprises a hydrochloric acid solution.

45. The assembly of claim 43, wherein the first chemical agent comprises sodium chlorite.

* * * * *